US009579401B2

(12) United States Patent
Melles

(10) Patent No.: US 9,579,401 B2
(45) Date of Patent: Feb. 28, 2017

(54) STAINING COMPOSITION

(75) Inventor: Gerrit Reinold Jacob Melles, Rotterdam (NL)

(73) Assignee: Medical Technology Transfer Holding B.V. (NL)

( * ) Notice: Subject to any disclaimer, the term of this patent is extended or adjusted under 35 U.S.C. 154(b) by 808 days.

(21) Appl. No.: 13/638,105

(22) PCT Filed: Apr. 1, 2011

(86) PCT No.: PCT/NL2011/050218
§ 371 (c)(1),
(2), (4) Date: Nov. 7, 2012

(87) PCT Pub. No.: WO2011/122947
PCT Pub. Date: Oct. 6, 2011

(65) Prior Publication Data
US 2013/0045167 A1 Feb. 21, 2013

(30) Foreign Application Priority Data

Apr. 1, 2010 (EP) .................................. 10159021
Jun. 3, 2010 (EP) .................................. 10164866

(51) Int. Cl.
A61K 49/00 (2006.01)
A61K 9/00 (2006.01)

(52) U.S. Cl.
CPC .......... *A61K 49/001* (2013.01); *A61K 49/003* (2013.01); *A61K 49/006* (2013.01); *A61K 49/0023* (2013.01); *A61K 49/0028* (2013.01); *A61K 49/0034* (2013.01); *A61K 49/0071* (2013.01); *A61K 9/0048* (2013.01)

(58) Field of Classification Search
None
See application file for complete search history.

(56) References Cited

U.S. PATENT DOCUMENTS

| 3,920,810 | A | | 11/1975 | Rankin | |
|---|---|---|---|---|---|
| 4,983,585 | A | * | 1/1991 | Pennell | A61F 9/007 514/57 |
| 5,585,469 | A | * | 12/1996 | Kojima et al. | 534/573 |
| 2003/0097117 | A1 | | 5/2003 | Buono | |
| 2006/0073184 | A1 | * | 4/2006 | Xia | A61F 9/0017 424/427 |
| 2006/0235068 | A1 | | 10/2006 | Snyder et al. | |
| 2011/0190728 | A1 | | 8/2011 | Lingenfelder et al. | |
| 2011/0194135 | A1 | | 8/2011 | Hamilton et al. | |

FOREIGN PATENT DOCUMENTS

| EP | 1132065 A1 | 9/2001 |
|---|---|---|
| JP | 2002514470 A | 5/2002 |
| JP | 2002514471 A | 5/2002 |
| JP | 2008522953 A | 7/2008 |
| JP | 2008543395 A | 12/2008 |
| WO | 86/02548 A1 | 5/1986 |
| WO | 96/32929 A1 | 10/1996 |
| WO | 99/58159 A1 | 11/1999 |
| WO | 9958159 A1 | 11/1999 |
| WO | 9958160 A1 | 11/1999 |
| WO | 0166053 A1 | 9/2001 |
| WO | 03043548 A1 | 5/2003 |
| WO | 2006062233 A1 | 6/2006 |
| WO | 2006133903 A2 | 12/2006 |
| WO | 2007130981 A2 | 11/2007 |
| WO | 2008032212 A2 | 3/2008 |
| WO | 2009120244 A1 | 10/2009 |
| WO | 2010078942 A2 | 7/2010 |

OTHER PUBLICATIONS

Albrecht et al (Probing the role of multicellular organization in three-dimensional microenvironments. Nat Methods. May 2006;3(5):369-75).*
Veritti et al (Dyes play vital role in vitreoretinal surgery. Ocular Surgery News Europe Edition, Mar. 2012).*
Foster, Robert E., et al., "Negative Indocyanine Green Staining of Epiretinal Membranes," Retina, Feb. 2002, pp. 106-108, vol. 22, No. 1, The Ophthalmic Communication Society, Inc.
Gonzalez-Tello, Pedro, et al., "Density and Viscosity of Concentrated Aqueous Solutions of Polyethylene Glycol," J. Chem. Eng. Data, 1994, pp. 611-614, vol. 39, American Chemical Society.
Kolacny, D.,et al., "Vitrectomy with Peeling of the Inner Limiting Membrane for Treating Diabetic Macular Edema," Bull. Soc. belge Ophtalmol., 2005, pp. 15-23, vol. 296.
Messmer, Elisabeth M., "Ultrastructure of epiretinal membranes associated with macular holes," Graefe's Arch Clin Exp Opthalmol, 1998, pp. 248-254, vol. 236, Springer-Verlag.
Nuyts, Rudy M. M. A., "Intraocular irrigating solutions: a comparison of Hatmann's lactated Ringer's solution, BSS and BSS Plus," Graefe's Arch Clin Exp Opthalmol, 1995, pp. 655-661, vol. 233, Springer-Verlag.
Yamaoka, Tetsuji, et al.,"Fate of Water-Soluble Polymers Administered via Different Routes," Journal of Pharmaceutical Sciences, Mar. 1995, pp. 349-354, vol. 84, No. 3, American Chemical Society and American Pharmaceutical Association.
Yoon, Hee-Seong, et al.,"Ultrastructural Features of Tissue Removed During Idiopathic Macular Hole Surgery," American Journal of Ophthalmology, 1996, pp. 67-75, vol. 22, No. 1.
A. Ueno, "Biocompatibility of Brilliant Blue G in a rat model of subretinal injection", Retina 2007, vol. 27, No. 4.
C. Veronese, "Photoxicity Associated to the Use of Brilliant Blue G in Vitreoretinal Surgery"—Abstract, 2010.
C.F. Snyder et al., Journal of Research of the National Bureau of Standards, vol. 53, No. 3, Sep. 1954.

(Continued)

Primary Examiner — Jake Vu
(74) Attorney, Agent, or Firm — Banner & Witcoff, Ltd.

(57) ABSTRACT

The invention is directed to a staining composition and to the use of the staining composition in staining ocular tissue. In a first aspect, the invention provides a staining composition comprising a vital dye and a density increasing compound chosen from the group consisting of water soluble polymers and small inert molecules.

25 Claims, 6 Drawing Sheets

(56) References Cited

OTHER PUBLICATIONS

E.T. Kareem, National Journal of Chemistry, 2006, vol. 22.
H. Enaida, "Brilliant Blue G selectively stains the internal limiting membrane ( . . . )", Retina 2006, vol. 26, No. 6.
Henrich, "Quantification of Contrast Recognizability During Brilliant Blue G (BBG) and Indocyanine Green (ICG) Assisted Chromovitrectomy", 2011.
M. Chakrabarti et al., Vital Dyes, Jun. 2008, p. 174-179, "Vital Dyes for Chromovitrectomy: Colours for the Vitreretinal Surgeon !!!"
M. Foroutan, Acta Chim. Slov., 2006, vol. 53.
Rodrigues c.s., "Intravitreal Staining of the Internal Limiting Membrane Using Indocyanine Green in the Treatment of Macular Holes", 2005.
Rodrigues c.s., "Mechanisms of intravitreal toxicity of indocyanine green due: implications for chromovitrectomy", 2007.
T. Hisatomi, "Staining Ability and Biocompatibility of Brilliant Blue G", 10 Arch Ophtalmol / vol. 124, Apr. 2006.
U. Spandau, H. Heimann, "Practical Handbook for Small-Gauge Vitrectomy", 2012.
Video presentation by dr. M.K. Schmid on the EVRS congress in Prague (title: "A new Method to Improve the Application of Dyes on the Retinal Surface Without Fluid-Air Exchange"), dated Sep. 9, 2008.
Vote, "Trypan blue-assisted vitrectomy", 2004.
W. Simawi, "The One-drop Technique for ILM Peeling", 2010.
Costa, Elaine de Paula Fiod, et al.,"Vital Dyes and Light Sources for Chromovitrectomy: Comparative Assessment of Osmolarity, pH, and Spectrophotometry," Investigative Ophthalmology & Visual Science, 2009, pp. 385-391, vol. 50, No. 1, Association for Research in Vision and Ophthalmology.
Lesnik Oberstein, Sarit Y., et al.,"Use of Heavy Trypan Blue in Macular Hole Surgery," Eye, 2010, pp. 1177-1181, vol. 24, Macmillan Publishers Limited.
Lesnik Oberstein, Sarit Y., et al.,"Heavy Trypan Blue Staining of Epiretinal Membranes: An Alternative to Infracyanine Green," Br J Ophthalmol, 2007, pp. 955-957, vol. 91.
Schmid, Martin K.,"A New Method to Improve Dye Application to the Retinal Surface during Vitrectomy," Retina, The Journal of Retinal and Vitreous Diseases, 2011, pp. 801-803, vol. 31, No. 4.
Office Action issued for corresponding Australian Patent Application No. 2015202819, dated Jul. 21, 2016.
van Nouhijs, Hester, et al. "Trypan-Blue-Stained Viscoelastic material for ophthalmic surgery," Journal of Cataract and refractive surgery, 2002, vol. 28, No. 9, p. 1713.

\* cited by examiner

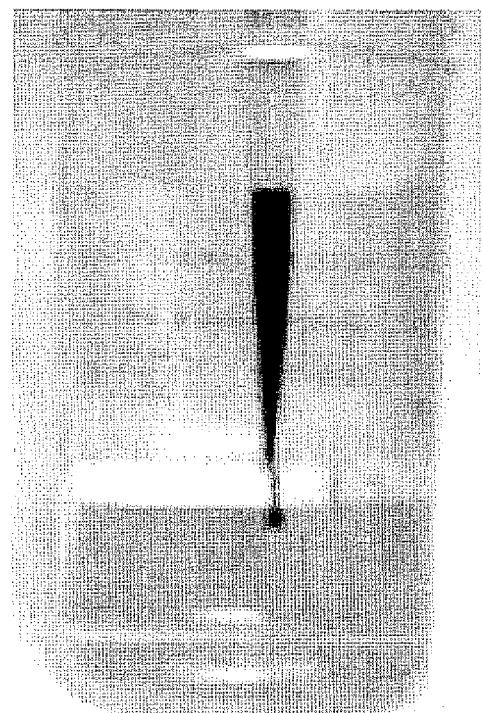
(a)
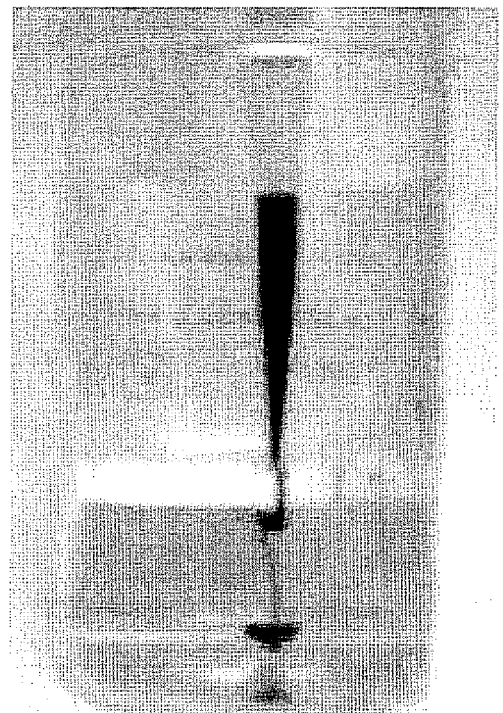
(b)
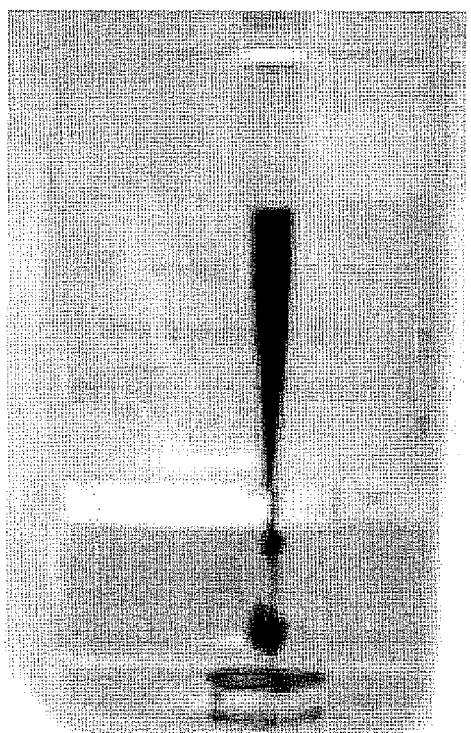
(c)
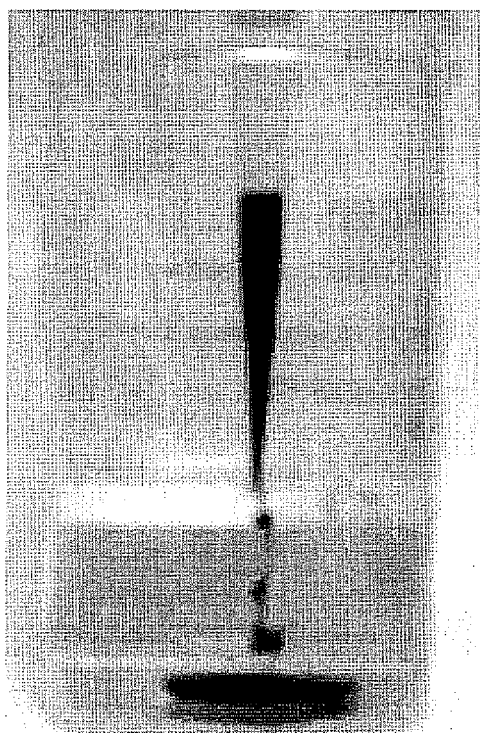
(d)
Fig. 2 a-d

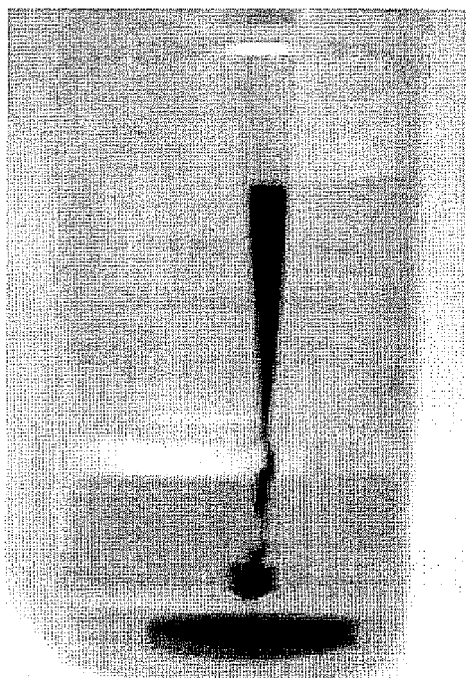
(e)
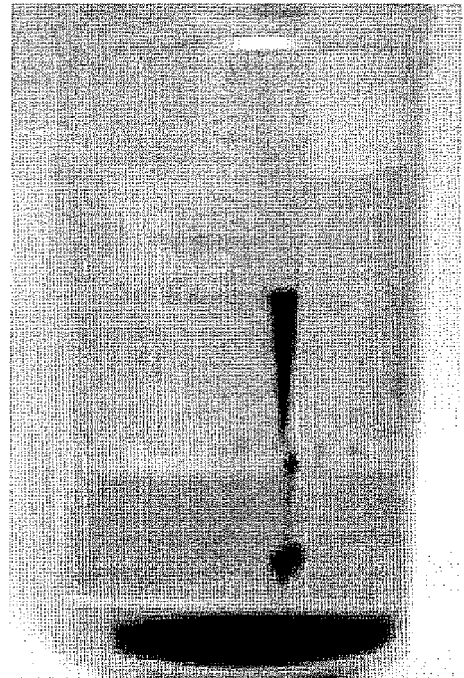
(f)
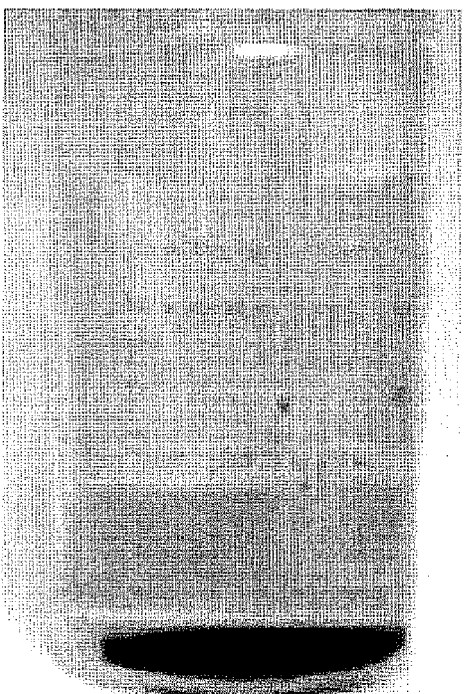
(g)
Fig. 2 e-g

STAINING COMPOSITION

RELATED APPLICATION DATA

This application is a National Stage Application under 35 U.S.C. 371 of co-pending PCT application PCT/NL2011/050218 designating the United States and filed Apr. 1, 2011; which claims the benefit of EP patent application number 10164866.5 and filed Jun. 3, 2010 and which claims the benefit of EP patent application number 10159021.4 and filed Apr. 1, 2010 each of which are hereby incorporated by reference in their entireties.

The invention is directed to a staining composition, a method for preparing the staining composition and to the use of the staining composition in staining ocular tissue.

To facilitate eye surgery, staining methods are used to distinguish one ocular tissue from the other.

For example, in vitreo-retinal surgery, the retinal membrane may be stained to visually distinguish it from surrounding or underlying healthy retinal tissue. Vitreo-retinal surgery is surgery that is aimed at providing a treatment of a disorder related to the retina, vitreous and/or macula. Examples of such disorders include retinal detachment, macular pucker, macular hole, macular degeneration, diabetic retinopathy, and uveitis. In vitreo-retinal surgery, often a retinal membrane is removed. Staining one of the retinal membranes makes it easier to distinguish different ocular tissues and remove a retinal membrane completely without damaging the surrounding retinal tissue.

Another example of eye surgery wherein staining is used to distinguish different ocular tissues is cataract surgery. An example of cataract surgery is cataract extraction, wherein the crystalline lens is removed from the eye. By selectively staining the lenticular material beneath the anterior lens capsule, the anterior lens capsule can be more easily distinguished, thus facilitating the surgery.

Dyes or dye mixtures suitable for staining used in ocular surgery should be non-toxic and physiologically acceptable. Furthermore, the dye should preferably be capable of staining an ocular tissue or an ocular tissue component without diffusing through said tissue or component, to prevent surrounding tissue from being stained as well.

WO-A-86/02548 discloses a composition to be used in ophthalmology that contains an aqueous solution of a high molecular polymer and a polymeric dye having a molecular weight higher than 10,000. The high molecular polymer is preferably a polysaccharide, such as dextran, a cellulose derivative, starch or a starch derivative, or a protein. Examples of synthetic polymers are also mentioned. The only examples mentioned for the dye are reactive dyes.

EP-A-1 132 065 discloses coloured visco-elastic compositions. Examples of visco-elastic compositions that are mentioned include hyaluronic acid, chondroitin sulfate, alginic acid, polysaccharides, polynucleotides, proteins, cellulose and cellulose derivatives and synthetic polymers such as acrylic acid and methacrylic acid polymers.

WO-A-99/58159 describes the use of a vital dye for staining a retinal membrane in an eye. Such use of a vital dye allows the surgeon to visually distinguish the retinal membranes from the underlying retina, so that the membranes can be better identified during surgery, for example to prevent the incomplete removal of the membranes, or damage to the retina itself. Examples of suitable vital dyes are trypan blue, trypan red, brilliant cresyl blue and indocyanine green.

WO-A-99/58160 describes a method for performing a capsulorhexis, a technique used to remove the lens capsule during cataract surgery, in which method a lens capsule is stained using at least one dye, which dye is capable of staining tissue without diffusing through said tissue. Examples of suitable dyes are trypan blue, trypan red and brilliant cresyl blue.

The staining compositions according to the prior art are typically applied to the surface of the ocular tissue to be stained. The staining composition will then be allowed to spread through this tissue by allowing the staining composition to sink onto or penetrate the tissue under the force of gravity.

The staining composition of the prior art has several disadvantages when used in eye surgery.

The disadvantages of the staining composition of the prior art are in particular related to rinsing of the eye tissue during eye surgery. During eye surgery most tissues have to be rinsed continuously with a saline rinsing solution to reduce the risks of inflammation, infection and tissue damage.

A first disadvantage of the composition of the prior art is that after applying such a composition to the eye tissue, rinsing may partially remove the dye. Consequently, the tissue may not be properly stained.

A further disadvantage is that the dye in the staining composition of the prior art may have the undesirable side-effect of also staining the rinsing solution. A stained rinsing solution obscures the visibility of the target tissue. Consequently, eye surgery can only be continued after the stained rinsing solution is completely washed out first. Furthermore, the stained rinsing solution may have an undesired staining effect on other tissues or in other parts of the eye.

A further disadvantage of the staining compositions of the prior art is that the staining composition may still partially diffuse through the ocular tissue to which the dye is applied. This decreases the sharp separation between the stained ocular tissue and the surrounding tissue. Consequently, a surgeon will have more difficulty to visually distinguish the stained ocular tissue from the surrounding tissue.

Object of the present invention is to overcome at least one of the disadvantages described above.

In a first aspect, this object is met by providing a staining composition comprising a vital dye and a density increasing compound chosen from the group consisting of water soluble polymers and small inert molecules.

The inventors realized that the disadvantages described above were mainly related to the slow interaction between the dye and the target tissue. They further realized that at least some of these disadvantages described above could be solved by decreasing the time it takes for the staining composition to sink onto or penetrate into the ocular tissue after being applied to the surface of such tissue.

Thus, it was found that by increasing the density of a staining composition, the time it takes for the staining compositions to sink onto or penetrate the ocular tissue when applied to the surface of such tissue was decreased. It was found that increasing the density of the staining composition could be achieved by using a water soluble polymer, in particular polyethylene glycol, or small inert molecules as one of the components of the composition.

It is a further advantage of the invention that the presence of the water soluble polymer or small inert molecule does not, or at least not to a significant detrimental extent, affects the stability of the vital dye. This is surprising, because most vital dyes are relatively unstable and adding compounds to a staining composition, such as a phosphate buffer, may increase the degradation rate of the vital dye. In accordance with the invention it has been found that this is not the case.

It has even been found that the stability of the vital dye may be increased by the presence of certain water soluble polymers or small inert molecules, for example the presence of polyethylene glycol (PEG). This beneficial effect has in particular been observed for a staining composition comprising trypan blue and polyethylene glycol.

Without wishing to be bound by any theory, it is assumed that both the pH of the staining composition and the water activity thereof play a role in the degradation of vital dyes. It is expected that the density increasing compound decreases the water activity in the staining composition, thus leading to a lower degradation rate of vital dyes.

The density increasing compound provides the staining composition of the invention with a higher density. The composition may therefore also be referred to as a weight enhanced staining composition. The staining composition of the invention thus provides for more precise targeting, for example by applying the dye more locally, more intense staining, reduced risk of undesired staining of other tissue (collateral staining) and/or reduced risk of staining the rinsing solution used during eye surgery.

The term "vital dye" as used herein refers to a dye which has a sufficient coloring, or staining capacity at a concentration which is physiologically and toxicologically acceptable. Hence, such a dye can be used in an (in-vivo) environment of living cells and tissues. In other words, the minimum amount of dye which is necessary to provide sufficient staining for a useful coloring to be visible should be low to such an extent that no, or hardly any, adverse toxic effects occur. Preferably, the dye is not, or at least hardly, toxic for the retina and adjacent structures. It is further preferred, that substantially no traces of the dye are present in the eye, shortly after the eye surgery procedure has been completed. As a result, there is hardly any risk of the patient experiencing any side-effects from the use of the dye.

The term "density" as used herein refers to the buoyant density. The presence of the density increasing compound thus increases the buoyant density of the staining composition compared to a staining composition where such a density increasing compound would be absent. The buoyant density of the staining composition may for example be calculated by taking the total weight of a certain volume of staining composition and subtracting thereof the total weight of ocular fluid displaced by said volume of staining composition.

The term "density increasing compound" refers to a compound chosen from the group consisting of water soluble polymers, in particular polyethylene glycol, and small inert molecules, which compound, when present in a staining composition, reduces the time it takes for the staining compositions to sink onto or penetrate the ocular tissue when applied to the surface of such tissue, in particular by increasing the buoyant density of the staining composition.

The term "ocular tissue" as used herein may refer to any tissue present in the eye. In particular, ocular tissue may refer to the retinal membrane of the eye and the lens capsule of the eye.

The term "retinal membrane" as used herein refers to both pathological retinal membrane tissue, partially pathological retinal membrane tissue and healthy retinal membrane tissue. Thus, the term "retinal membrane" encompasses e.g. proliferative vitreoretinopathy (PVR) membranes, epiretinal membranes, the (thickened or altered) inner limiting membrane (ILM) and vitreous membranes, as well as elements or components of these membranes.

The term "underlying or surrounding tissue" may refer to tissue that is adjacent or underneath to the ocular tissue to be stained. In particular, surrounding tissue may refer to underlying tissue of the ocular tissue to be stained, to visually distinguish the pathological tissue from the tissue not primarily affected by disease.

BRIEF DESCRIPTION OF THE DRAWINGS

FIGS. 2(a)-(g) are pictures taken at 0 s, 0.15 s, 1.06 s, 1.94 s, 5.06 s, 10.15 s, and 12.91 s after starting the release of the staining composition from a pipet.

Figure 1:
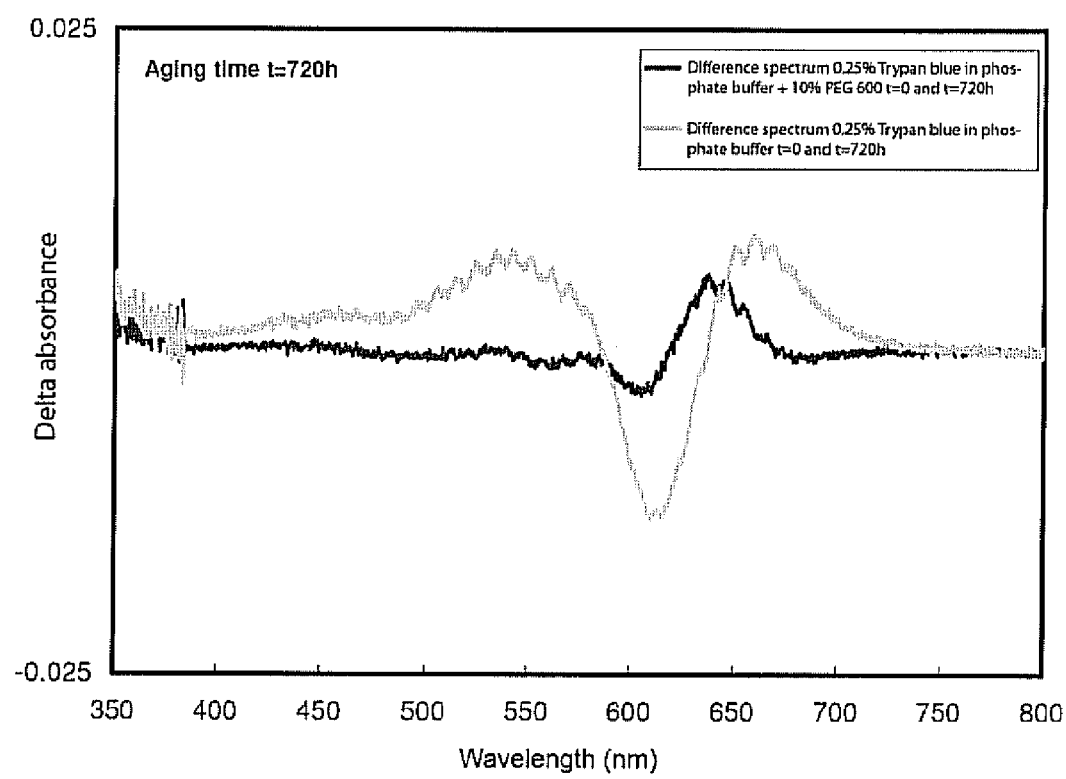
FIG. 1 is a graph depicting the concentration of trypan blue in a freshly made staining composition and the concentration of trypan blue in a second staining composition comprising PEG.

Preferably, the density increasing compound does not, or at least not significantly, affect the staining properties of the vital dye used.

The density increasing compound is preferably non-ionic due to the difficulty of controlling the osmolarity of staining compositions comprising ionogenic density increasing compounds.

In case the density increasing compound is a polymer, water soluble polymers are preferred. Preferably, such a water soluble polymer is selected from the group consisting of polyethylene oxides and their derivatives such as ethers and esters (PEG), polypropylene oxides and their derivatives such as ethers and esters (PPG), polyvinyl alcohols and their derivatives such as ethers and esters (PVA), polyvinyl methyl ethers, polyethylene imine, polyvinyl pyrrolidones (PVP), polyvinyl oxazolidine, polyvinyl methyl oxazolidine, dendrimers and combinations thereof. Dendrimers that may be used are for example polyamidoamine dendrimers (PAMPAM), in particular $3^{rd}$ and $4^{th}$ generation PAMAM to which one or more PEG polymers (e.g. PEG 550) are attached.

In one embodiment, the water soluble polymer is selected from the group consisting of polyethylene oxides and their derivatives such as ethers and esters (PEG), in a preferred embodiment the water soluble polymer is polyethylene glycol. The PEG preferably has a molecular weight in the range of 600-100,000, more preferably in the range of 2,000-10,000. It was found that using PEG as the water soluble polymer may give the additional advantage of decreasing, or at least not increasing, the degradation rate of the dye. This effect was found to be particularly strong for trypan blue.

It was further found that the presence of glucose and/or maltose in a staining composition significantly increased the degradation rate. Although a staining composition comprising glucose and/or maltose did also increase the density and/or viscosity of the staining composition, such a composition was found to be less suitable for use in eye surgery than the composition of the invention. A staining composition comprising glucose and/or maltose, in addition to its chemical instability, mixes relatively fast with rinsing solution compared to the staining composition of the invention.

A small inert molecule that may be suitably used as a density increasing compound is for example a halogenated organic compound. Preferably, the halogenated organic compound is a brominated or iodinated organic compound, due to the high mass of bromine and iodine. More preferably, the halogenated organic compound is a iodinated organic compound. These compounds are also used in X-ray contrast applications. Examples of iodinated organic compounds are iodixanol or iodinated benzoic acid, which iodinated benzoic acid may be substituted with one or more hydrophilic side chains. An example of this last type of molecule is 5-N(N-2,3-dihydroxypropylacetamido)-2,4,6-tri-iodo-N,N'-bis(2,3-dihydroxypropyl) isophtalamide (available under the name Nycodenz®).

If the molecular weight of the density increasing compound is chosen too small, the density increasing compound may not be sufficiently effective in increasing the density of the staining composition. Therefore, the density increasing compound preferably has a molecular weight of at least 50 g/mol, more preferably at least 100 g/mol, even more preferably at least 300 g/mol, even more preferably at least 600 g/mol, even more preferably at least 800 g/mol, even more preferably at least 1000 g/mol. For example, PEG600 and Nycodenz®, having a molecular mass of 821 g/mol, may both be suitably used as a density increasing compound. When using PEG as a density increasing compound, the molecular weight of PEG is preferably 600 g/mol or higher for reasons of osmolarity (see also hereinbelow). Effective amounts of smaller PEG polymers in the staining composition of the invention may result in an osmolarity that may be too high.

The density increasing compound preferably has a molecular weight of at most 500,000 g/mol, more preferably at most 100,000 g/mol, most preferably at most 40,000 g/mol. If the molecular weight of the density increasing compound is chosen too high, e.g. above 40,000 g/mol, the body may have difficulty eliminating the density increasing compound from the body, in particular in case of polymers (see also "Fate of water-soluble polymers administered via different routes, Tetsuji Yamaoka, Yasuhiko Tabata, Yoshito Ikada, J. Pharm. Sci. 84 (3), p 349-354"). An additional disadvantage in case polymers having a high molecular weight are used as the density increasing compound is that a staining composition comprising polymers having a high molecular weight may be too viscous, which may cause problems when applying the staining composition and/or later when present in the stained tissue.

The molecular mass of small inert molecules, such as for example iodixanol, may be determined using mass spectrometry. The molecular mass of the water soluble polymers may be determined using for example size-exclusion chromatography coupled with multi-angle laser light scattering detection.

The staining composition preferably has a density of more than 1003 kg·m$^{-3}$ and less than 1040 kg·m$^{-3}$, more preferably a density of 1004-1026 kg·m$^{-3}$, measured at a temperature of 298 K. This density is higher than staining compositions of the prior art, which typically have a density of 1003 kg·m$^{-3}$ at 298 K. The density may be measured using a pycnometer, as described in "*Density and Viscosity of Concentrated Aqueous Solutions of Polyethylene Glycol*" by Pedro Gonzalez-Tello, Fernando Camacho, and Gabriel Bllzquez J. Chem. Eng. Data 1994, 39, 611-614.

Preferably, a vital dye is used that is capable of staining tissue without diffusing through said tissue.

Particularly good results have been achieved using a vital dye having the formula

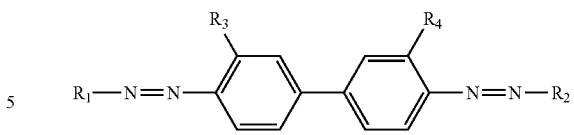

wherein $R_1$ and $R_2$ are the same or different arylgroups, and wherein $R_3$ and $R_4$ are independently chosen from hydrogen, methyl, ethyl, methoxy, amino, hydroxyl, and sulfonate. $R_1$ and $R_2$ are preferably the same and formed by substituted naphtylgroups. Preferably, the naphtylgroups are substituted with one or more of sulfonate groups, amino groups and hydroxyl groups. These dyes have been found to bind predominantly to fibrous tissue, such as the tissue of the retinal membranes, which makes them particularly suitable for application in vitreo-retinal surgery.

Preferably, the dye is chosen from the group consisting of methylene blue (MB), brilliant blue G (BBG), brilliant blue R (BBR), patent blue V, Chicago Sky Blue 6B (also known as Direct Blue 1 and Pontamine Sky Blue), trypan blue (TB), trypan red, brilliant crysyl blue, indocyanine green, light green SF yellowish (LG), phenol red, chlorophenol red-beta-D-galactopyranoside (CPRG), rose bengal (4,5,6,7-tetrachloro-2',4',5',7'-tetraiodofluorescein), phloxine B, safranin T, and combinations thereof. It has been found that these dyes provide a clearly visible staining at very low amounts. Also, they have an advantageous toxicity profile.

Preferably, the dye comprises a first and a second dye, wherein the first dye is trypan blue (TB) or Chicago Sky Blue 6B and the second dye is chosen from the group consisting of brilliant blue G (BBG), light green SF yellowish (LG), phenol red, chlorophenol red-beta-D-galactopyranoside (CPRG), rose bengal (4,5,6,7-tetrachloro-2',4',5',7'-tetraiodofluorescein), phloxine B and safranin T. More preferably, the dye is a combination of trypan blue (TB) and brilliant blue G (BBG).

The presence of trypan blue and a second dye as defined above in the staining composition has the advantage that it provides for staining different ocular tissues with different dyes, thereby making it easier to visually distinguish the different ocular tissues from each other during surgery. In particular, trypan blue will mainly colour the epiretinal membrane, while the second dye will mainly stain the inner limiting membrane.

The weight ratio of the first dye (trypan blue) to the second dye in the dye of the staining composition is preferably between 1:1 and 100:1, more preferably between 2:1 and 25:1, even more preferably between 4:1 and 15:1. The staining composition may be provided in solid form, where a liquid, e.g. an aqueous solution can be added later to prepare a fresh liquid composition for use in eye surgery.

The staining composition of the invention may be a liquid staining composition, in particular an aqueous staining composition. In this case, the staining composition is preferably an aqueous solution or a colloidal dispersion. The density increasing compound may be dissolved in the liquid staining composition or dispersed in the liquid staining composition as colloidal particles.

The concentration of the density increasing compound in the liquid staining composition is preferably at least 4 g/L, more preferably 10 g/L, more preferably at least 20 g/L, even more preferably at least 40 g/L.

In case the density increasing compound is a water soluble polymer, in particular PEG, the concentration is preferably is at least 1 wt. % and more preferably 2-10 wt.

%, more preferably 3-6 wt. % based on the total weight of staining composition. The concentration of density increasing compound is preferably less than 50 wt. %, based on the total weight of staining composition.

It was found that the viscosity of the liquid staining composition may influence the rate of mixing with the rinsing liquid. A liquid staining composition having a sufficiently high viscosity may show a desirable low mixing rate with the rinsing liquid, thereby allowing for a particular high and narrowly localized concentration of the dye upon application to the surface of the tissue to be stained. This is desirable, because it allows for a decrease in the time it takes for the staining compositions to penetrate the ocular tissue when applied to the surface of such tissue and/or reduce the risk of undesired staining of surrounding tissue. Therefore, the viscosity of the liquid staining composition is preferably at least 2.0 mPa·s, more preferably at least 2.2 mPa·s, even more preferably 2.5 mPa·s. Furthermore, the viscosity of the staining composition is preferably less than 18 mPa·s, more preferably less than 9 mPa·s. A staining composition with a too high viscosity may result in a staining rate that is too low, due to the diffusion rate of a vital dye in a viscous composition being lower in a composition having a higher viscosity than in a composition with a lower viscosity. The viscosity as used herein in particular refers to the dynamic viscosity. Viscosity values were determined using a rheometer at a temperature of 298 K.

The staining composition may further comprise a salt. The liquid staining composition is preferably isotonic with ocular fluid. For this purpose, the liquid staining composition may comprise a salt to adjust its osmolarity to a suitable value. The staining composition of the invention preferably has an osmolarity between 250 and 400 mosmol/L, preferably 300-330 mosmol/L, for example 315 mosmol/L. The skilled person will be able to calculate the amount of salt needed to achieve this.

The salt may be chosen from the group consisting of sodium chloride, potassium chloride, calcium chloride, magnesium chloride, or a combination thereof. To provide the staining composition with a salt, the staining composition may comprise a salt solution. Suitable examples are Balanced salt solution or Hartmann's lactated Ringer's solution (see also Nuijts RMMA, Edelhauser H F, Holley G P, "Intraocular irrigating solutions: a comparison of Hartmann's lactated Ringer's solution, BSS and BSS plus", Clin. Exp. Ophtamol., vol. 233 (1995), pp. 655-661).

It is further preferred that the liquid staining composition has a neutral pH, i.e. a pH of 6.5-7.5. The staining composition may therefore comprise a buffer, preferably a salt buffer, which has the properties to be of use in ophthalmic applications. An example of a suitable buffer is phosphate buffered NaCl, commercially available at NPBI, Emmer-Compascuum, The Netherlands.

The concentration of the dye in the liquid staining composition is preferably 0.001-2 wt. %, more preferably 0.01-1 wt. %, even more preferably 0.1-0.5 wt. % based on the total weight of the staining composition. Within this range, the concentration may be adapted to the toxicity and coloring characteristics of the dye used. It is preferred that such an amount is chosen that an optimal staining effect is achieved, while at the same time the risk of possible damage to the eye or any part thereof due to the toxicity of the dye is minimized.

For example, a liquid staining composition may comprise 0.05-0.5 wt. % TB, 0.01-0.1 wt. % BBG and 1-10 wt. % water soluble polymer, for example PEG, based on the total weight of the staining composition.

For certain applications, for example in some applications wherein the staining composition is applied to the anterior lens capsule, it may be desirable that the staining composition is a dispersion or a viscous or viscoelastomeric solution. For example, the staining composition may comprise hyaluronic acid (see WO-A-96/32929). It will be well within the standard expertise of the skilled person to select a suitable form for the solution. For instance, a higher viscosity may be desired in order to reduce the tension on the lenticular capsule during capsulorhexis or to protect the cornea.

Each component in the staining composition preferably has a concentration in the staining composition that is physiologically and toxicologically acceptable. In other words, the minimum amount of each component in the staining composition should be sufficiently low such that no, or hardly any, adverse toxic effects occur. Preferably, each component in the staining composition is not, or at least hardly, toxic for the retina and adjacent structures. It is further preferred, that the content of each component in the staining composition present in the eye, shortly after the eye surgery poses hardly any risk of the patient experiencing any side-effects from the use of the staining composition.

The invention is further directed to a method for preparing a staining composition, comprising the step of dissolving a vital dye and a density and viscosity increasing compound in a liquid.

The vital dye and density increasing compound used in the method of the invention are as described hereinabove. The liquid used in the method of the invention is preferably chosen from the group consisting of water, a salt solution or a buffer, such as a salt buffer. Examples of suitable salt solutions or buffers are described hereinabove.

The method may further comprise the step of dissolving a salt in the liquid to adjust the osmolarity of the liquid to a value between 250 and 400 mosmol/L, preferably 315 mosmol/L.

The staining composition according to the invention may be used in the treatment of staining an ocular tissue or part of an ocular tissue. Staining of at least part of an ocular tissue may be used in many types of ocular surgery to facilitate the work of the surgeon by making it easier for him to visually distinguish one ocular tissue from the other.

In particular, the staining composition of the invention may be used to stain a first ocular tissue so as to distinguish it from a second ocular tissue. The first ocular tissue may be the surrounding or underlying tissue of the second tissue. Alternatively, the second ocular tissue may be the surrounding or underlying tissue of the first tissue.

The treatment of staining at least part of an ocular tissue may be part of an eye surgery, for example vitreo-retinal surgery or cataract extraction. Such surgery may be conducted to treat various conditions. Surgery that is aimed at providing a treatment of a disorder related to the retina, vitreous and/or macula is referred to as vitreo-retinal surgery. Examples of such conditions include retinal detachment, macular pucker, macular hole, macular degeneration, diabetic retinopathy, and uveitis. Eye surgery may also be conducted to treat cataract. This condition may be treated by a surgical procedure called cataract extraction.

The staining composition of the invention may be used in glaucoma surgery visualize Schlemm's canal and/or to evaluate if the conjunctival filtering bleb is potent. Examples of glaucoma surgery are trabeculectomy and the introduction a glaucoma drainage implant such as a Baerveldt implant.

The staining composition of the invention may be used in a method or procedure for performing retinal membrane removal, wherein the staining composition is used to stain the retinal membrane. The retinal membrane removed in such a method or procedure may for example be the proliferative vitreo-retinal membrane, the epiretinal membrane or the inner limiting membrane.

The staining composition of the invention may also be used in a method or procedure for performing a capsulorhexis, wherein a lens capsule of an eye is stained using the staining composition. The staining composition may in this case be capable of staining tissue without diffusing through said eye.

It may be important to note that in accordance with the invention the dye is not used to have a diagnostic or therapeutic effect. The contrast produced by staining of the tissue is only visible and/or useful in combination with the actual surgical handling, e.g. removal of the tissue. In other words, the dye is not applied onto the tissue make or confirm a diagnosis, since the transparency of the ocular media allows medical professionals to establish the type of pathology (i.e. to come to a diagnosis) before the surgery. Also, the dye does not have any therapeutic effect and does not act as an adjuvant. The purpose of staining the tissue is merely to produce a contrast between different tissue structures during a surgical procedure.

In the normal eye, the retina is located in the posterior segment of the eye, behind the corpus vitreum. The retina is a thin, translucent membrane resting on a single layer of pigmented epithelium, extending from the ora serrata to the optic disc. It consists of photoreceptor cells (rods and cones), which are connected to neuron pathways terminating in nonmyelinated fibers. These are combined to form the optic nerve. The innermost structure of the retina is the membrana limitans interna.

The vitreous is a clear, transparent, semi-solid gel which occupies about two thirds of the volume of the globe extending from the lens to the optic disc. It is a connective tissue space with the greater portion of the space made up of intercellular collagen and hyaluronic acid networks. The vitreous is in close contact with the epithelium of the pars plicata and pars plana, ora serrata and the internal limiting membrane of the retina as far as the optic disc. The vitreous base represents the most solid attachment of the vitreous to the wall of the eye. It straddles the ora extending anteriorly on the pars plana over 1.5 to 2 mm and posteriorly on the retina over 3 to 4 mm.

Retinal detachment typically occurs in older people. When people grow older the vitreous body may shrink and detach from the retina. In effect, the retina peels away from the vitreous support tissue, which may lead to vision loss and even blindness. Most retinal detachments are a result of a retinal break, hole, or tear. These retinal breaks may occur when the vitreous gel pulls loose or separates from its attachment to the retina, usually in the peripheral parts of the retina. Once the retina has torn, liquid from the vitreous gel can pass through the tear and accumulate behind the retina. The build-up of fluid behind the retina is what separates (detaches) the retina from the back of the eye. As more of the liquid vitreous collects behind the retina, the extent of the retinal detachment can progress and involve the entire retina, leading to a total retinal detachment.

Retinal detachments may be repaired in a procedure called a vitrectomy combined with a scleral buckle. In a vitrectomy, small openings are made through the sclera to allow positioning of a fiberoptic light, a cutting source (specialized scissors), and a delicate forceps. The vitreous gel of the eye is removed and replaced with a gas to refill the eye and reposition the retina. The gas eventually is absorbed and is replaced by the eye's own natural fluid. In addition or alternatively, a retinal detachment may be managed with scleral buckling, that involves sealing of the hole or tear in the retina, either with diathermy (an electric current which heats tissue), a cryoprobe (freezing), or a laser. This results in formation of scar tissue around the retinal tear to keep it permanently sealed, so that fluid no longer can pass through and behind the retina. A scleral buckle, which is made of silicone, plastic, or sponge, is then sewn to the outer wall of the eye (the sclera). The buckle is like a tight cinch or belt around the eye. This application compresses the eye so that the hole or tear in the retina is pushed against the outer scleral wall of the eye, which has been indented by the buckle. The buckle may be left in place permanently. It usually is not visible because the buckle is located half way around the back of the eye (posteriorly) and is covered by the conjunctiva (the clear outer covering of the eye), which is carefully sewn (sutured) over it. Compressing the eye with the buckle also reduces any possible later pulling (traction) by the vitreous on the retina.

Retinal detachments may be associated with proliferative vitreoretinopathy (PVR). PVR is the most common complication of a retinal detachment and occurs approximately 8-10% of patients who develop a retinal detachment. Proliferative vitreoretinopathy is the formation of scar tissue within the eye. The scar tissue forms in sheets or membranes on the retina and cause it to contract. This marked contraction pulls the retina toward the center of the eye and detaches and distorts the retina severely. PVR membranes typically consist of retinal pigment epithelial, glial and other cells. They have to be removed by membrane peeling during repair of a retinal detachment.

A macular pucker is also known as an epiretinal membrane, pre-retinal membrane, cellophane maculopathy, retina wrinkle, surface wrinkling retinopathy, pre-macular fibrosis, and internal limiting membrane disease. It is similar to PVR in that scar tissue is formed between the vitreous body and the retina as a result of shrinkage of the vitreous body. In the case of a macular pucker, the scar tissue is located in the center of the eye's light-sensitive tissue, the macula. Where the vitreous pulls away from the retina, there is microscopic damage to the retina's surface. The retina begins a healing process to the damaged area and forms scar tissue, or an epiretinal membrane, on the surface of the retina. This scar tissue is firmly attached to the retina surface. When the scar tissue contracts, it causes the retina to wrinkle, or pucker, usually without any effect on central vision. However, if the scar tissue has formed over the macula, our sharp, central vision becomes blurred and distorted.

Epiretinal membranes can be removed or peeled through the sclera. Usually in this procedure, the vitreous is replaced at the same time with clear fluid, in a vitrectomy.

A macular hole is a small break in the macula. When the vitreous body shrinks and pulls away from the retinal surface, natural fluids fill the area where the vitreous has contracted. If the vitreous body is firmly attached to the retina when it pulls away, it can tear the retina and create a hole at the location of the macula. This is called a macular hole. Also, once the vitreous body has pulled away from the surface of the retina, some of the fibers can remain on the retinal surface and can contract. This increases tension on the retina and can lead to a macular hole. In either case, the fluid that has replaced the shrunken vitreous can then seep through the hole onto the macula, blurring and distorting central vision.

Sometimes macular holes are associated with epiretinal membranes which may exert tangential traction on the retina. Bregsen et al. (Klin. Monatsbl. Augenheilkd., 1995, 206(1):2-12) proposed that the main cause for idiopathic senile macular holes is tangential traction induced by a thin epiretinal membrane. On the basis of the similar ultrastructure of epiretinal membranes associated with macular holes and simple epiretinal membranes it has been postulated that there is a common pathogenesis for macular holes and macular pucker (Messmer et al., Graefe's archive for clinical and experimental ophthalmology, 1998, 236(4):248-254).

Macular holes are generally treated by performing a vitrectomy wherein the vitreous body is removed to prevent it from pulling on the retina (release of intravitreous traction) and replaced with a bubble containing a mixture of air and gas. The bubble acts as an internal, temporary bandage that holds the edge of the macular hole in place as it heals. In case the macular hole is associated with epiretinal membranes, these will be removed during the vitrectomy.

In the late 1990's it has been proposed to treat macular holes by not only performing a vitrectomy with removal of epiretinal membranes, but by additional removal of the inner limiting membrane (ILM). The first to describe this were Yoon et al. (Am. J. Ophthalmol., 1996, 122:67-75). They intentionally removed the inner limiting membrane primarily to ensure complete removal of epiretinal membranes. Although the ILM has no inherent contractile properties, it was believed to act as a scaffold for contractile tissue to exert tangential traction on the retina. In 1997, Eckardt et al. (Ophthalmologe, 1997, 94:545-551) have observed that the thickness of the ILM may vary greatly. They could not exclude that the ILM may be thicker in patients having a macular hole and that the increased thickness has a pathological nature.

Recently, ILM peeling has become more widespread in macular hole surgery. Investigations (i.e. those by Yoon et al. and Eckardt et al., referred to above) proved that ultrastructural features of tissue removed during macular hole surgery showed cells with myofibroblastic differentiation on the ILM, which cells could play a role in the formation and enlargement of macular holes through contraction on the surface of the ILM. Brooks Jr. compares surgical results with and without ILM peeling and concludes that ILM peeling significantly improves visual and anatomical success in all stages of recent and chronic macular holes, particularly for large macular holes (>300 µm).

Another condition for which ILM peeling has been proposed as a part of a treatment by vitrectomy is diabetic macular edema (see Kolacny et al., Bull. Soc. Beige Ophthalmol., 2005, 296:15-23). Macular edema is a major cause of visual loss in patients with diabetes. In the past, it was usually treated with laser photocoagulation on focal leaking microaneurysms or grid treatment on areas of diffuse macular edema. Kolacny et al. report that vitrectomy with ILM peeling may be beneficial treatment as well.

It may be beneficial to stain a first ocular tissue to visualize a second tissue surrounding or underlying the first ocular tissue. For example, the ILM may be stained in order to visualize an epiretinal membrane. This technique, which is called 'negative staining', was developed for dyes which are more suitable for visualizing the ILM than epiretinal membranes, such as indocyanine green. By staining the first tissue, a second tissue that partially covers it becomes visible because it is the unstained tissue (see Foster et al., Retina, 2002, 22:106-108). Accordingly, a staining composition may be used to stain a retinal membrane in order to visualize a different structure in the eye to facilitate removal of that different structure.

A cataract may develop due to aging or to a wide variety of ocular or systemic pathological disorders or diseases. When a cataract develops, the lens substance becomes less transparent.

In the normal eye, the crystalline lens is located behind the iris, and in front of the corpus vitreum. The lens is transparent, biconvex, accounts for about 20 diopters of convergent refractive power of the eye, and it is composed of a capsule that encloses and encompasses the lens substance, i.e. the lens epithelium, the cortex, and the nucleus. A ring of zonular fibers, that extend from the ciliary body to the anterior part of the lens capsule, keeps the lens positioned within the eye.

The capsule is an elastic, type IV collagen basement membrane produced by the lens epithelial cells. The thickness of the capsule varies from 4-24 µm, with a thickness of about 14 µm at its anterior part, 24 µm at its equatorial part, and about 4 µm at its posterior part. Because of its transparency, and because its refractive index nearly equals the lens substance, the lens capsule can not be discriminated from the lens substance, except with the use of a slit-lamp at high magnification.

Portions of the lens substance affected by cataract may differ with the type of disorder, but in most cases the optical and/or refractive functions of the lens are compromised, for example a decreased visual acuity, a decreased contrast sensitivity, an accommodation loss, etc.

To restore the optical pathway, cataract surgery may be performed to remove the opaque lenticular mass. Although various surgical techniques are available, extracapsular cataract extraction techniques, the Blumenthal technique, or phacoemulsification are most often used. With all techniques, the anterior chamber of the eye is opened through a peripheral corneal, limbal or scleral incision, the anterior lens capsule is opened, and the lens substance is removed, while leaving the peripheral rim of the anterior lens capsule as well as the capsular equatorial and posterior portions in-situ. The empty lens capsule forms a capsular "bag" that can be used to support a synthetic intraocular implant lens (IOL), so that an IOL is positioned "in the bag".

Various techniques are used to open the anterior lens capsule, i.e. the excision of a portion of the anterior lens capsule, with or without the use of a viscous or viscoelastomeric substance, for example the can-opener technique, the envelop technique, the capsulotomy, and the continuous circular capsulorhexis. To visualize the capsular defect during the opening of the capsule, the red fundus reflex, the co-axial light of an operating microscope that is reflected from the posterior pole of the eye, is commonly used. When retroillumination is absent, for example with dense cataracts, heavily pigmented fundi or a combination of both, it is often not or only hardly possible to discriminate the anterior capsule from the underlying lens tissue.

Visualization of the defect in the anterior capsule during the opening of the lens capsule is an important step in the surgical procedure, because the mechanical traction forces which the capsule can withstand during surgery, vary with the configuration of the capsular opening. For example, in phacoemulsification a continuous circular capsulorhexis is commonly performed, because a circular configuration of the capsular opening can withstand best the surgical manipulations within the lens capsule during the removal of the lens substance. Improper visualization of the anterior lens capsule during the performance of a capsulorhexis may be responsible for a risk of a radial tear toward or beyond the equator of the lens capsule, and associated complications, for example vitreous loss, or a dropped nucleus.

Furthermore, in a subsequent phase of the surgery the outline of the opening in the anterior lens capsule is often difficult to visualize. During the removal of the lens substance in phacoemulsification a useful red fundus reflex is nearly always absent, because the lenticular tissue becomes opaque. However, during phacoemulsification it still is important that the rim of the capsulorhexis is not damaged, so that the capsular integrity is maintained during the surgical manipulations within the capsule. For example, an inadvertent touch of the rim with the tip of the phacoemulsification hand piece or an overextension of the capsule during dividing the lenticular substance, may damage the rim of the capsulorhexis. Again, the damaged rim may give a greater risk of a radial tear toward the equator and associated complications, especially because the damage to the rim of the capsulorhexis may not be noticed during surgery.

During implantation of an IOL, the rim of the anterior capsule must be visualized to place the haptics of the IOL in between the anterior and posterior portions of the lens capsule. In this phase of the surgery, the anterior capsular rim can often be seen with the use of the red fundus reflex. To determine if a haptic (s) is positioned underneath the anterior capsular rim, the IOL is manipulated in such a way that the displacement of the capsular rim by the haptic or optic of the IOL indicates the position of the IOL relative to the capsule. In cases where a useful red fundus reflex is absent, as mentioned above, it becomes difficult to determine the position of the IOL relative to the capsule and staining may be used to reduce the risk of the IOL being inserted in the area between the iris and the anterior lens capsule, for example the ciliary sulcus.

The invention is further directed to a method for staining an ocular tissue or part thereof, comprising the steps of
  applying the staining composition of the invention to the surface of the ocular tissue or part of the ocular tissue; and
  allowing the staining composition to sink onto or penetrate the ocular tissue or part of the ocular tissue.

The present invention will be further illustrated by the following example.

EXAMPLE 1

Density Measurements

The density of a 17% PEG 600 solution, a 0.9% NaCl solution and a 4% PEG3350 were determined using a pycnometer. Thus, the density of the PEG600 solution was determined to be 1013 kg·m$^{-3}$, the density of the NaCl solution 1003 kg·m$^{-3}$ and the density of the PEG3350 solution 1004 kg·m$^{-3}$ at 298 K. These results demonstrate that the presence of PEG in a solution increases its density.

EXAMPLE 2

Sinking Rate Ex Vivo

100 µL of a staining composition comprising 0.15 wt. % trypan blue (TB) and 10 wt. % polyethylene glycol having a molecular weight of 3350 g/mol (PEG 3350) was released in approximately 13 s by a pipet in a glass beaker filled with 4 mL phosphate buffered saline.

The experiment was recorded on video and the sinking behaviour was evaluated by visual inspection. Pictures were taken at 0 s, 0.15 s, 1.06 s, 1.94 s, 5.06 s, 10.15 s and 12.91 s after starting the release of the staining composition from the pipet, as illustrated in FIGS. 2(a)-2(f), respectively.

Furthermore, it was observed by visual inspection that the staining composition did not mix with the contents of the glass beaker. It was further observed that the staining composition remained localized to the area on which the dye was applied, viz. on the bottom of glass beaker, even after the dye holder was empty, as can be seen in FIG. 2(g).

The observed behaviour is desirable, because the narrow localization and lack of mixing allows for fast penetration in the ocular tissue when applied to the surface of such tissue and/or a reduced risk of undesired staining of surrounding tissue. The experiment thus demonstrates that the staining composition is not prone to staining the rinsing solution and/or surrounding ocular tissue.

EXAMPLE 3

Sinking In Vivo

The staining composition of the invention is administered on the target tissue 'under air', i.e. the vitrous cavity is completely filled with air, or 'under balanced salt solution', i.e. the vitreous cavity is completely filled with balanced salt solution. The dye remains localized to the area on which the dye is applied. After removing all excess dye, the target tissue is stained, allowing for selective removal of the internal limiting membrane or epiretinal membranes.

EXAMPLE 4

Dye Degradation

Degradation of the vital dye trypan blue in two staining compositions was measured over time. The first staining composition comprised 0.25 wt. % trypan blue and a phosphate buffered salt solution (0.25 wt. % disodium monophosphate 12H$_2$O, 0.036 wt. % monosodium diphosphate 2H$_2$O and 0.8 wt. % sodium chloride). The second staining composition comprised 0.25 wt. % trypan blue, 17 wt. % polyethylene glycol 600 (PEG600) and a phosphate buffered salt solution (0.25 wt. % disodium monophosphate 12H$_2$O (0.25 wt. %), monosodium diphosphate 2H$_2$O (0.036 wt. %))

Sodium chloride was present in the buffer of the first staining composition to provide the first staining composition with a suitable osmolarity value. The buffer in the second staining composition did not comprise any sodium chloride, because the presence of PEG in the staining composition already resulted in a suitable value for the osmolarity.

The two staining compositions were incubated at 70° C. for 30 days. The concentration of trypan blue in the two samples was measured by subtracting the absorption spectrum taken after 720 hours of these samples from the absorption spectrum of a freshly made staining composition (used as a blank).

The results of the experiment are shown in FIG. 1. FIG. 1 shows the measured absorption difference with the blank. The absorption difference of the second staining composition (comprising PEG) is clearly smaller than the absorption difference of the first staining composition. Thus, the experiment demonstrates that trypan blue was degraded considerably faster in the first staining composition compared to the second staining composition comprising polyethylene glycol.

EXAMPLE 5

Stability of Trypan Blue and Brilliant Blue G in Polymer Solutions

Figure 3:
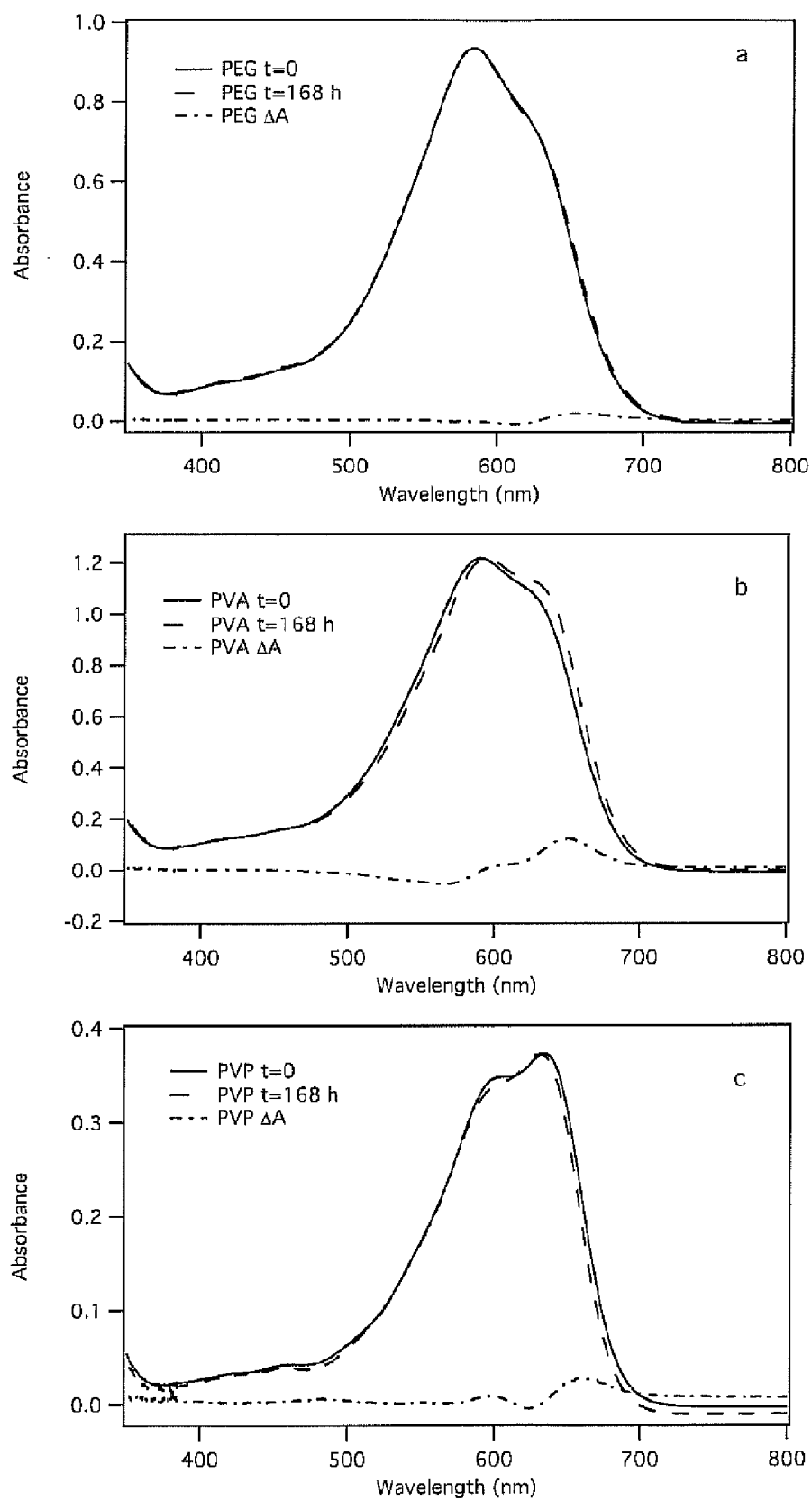
FIG. 3 graphically depicts the normalized absorbance of a trypan blue solution.
Figure 4:
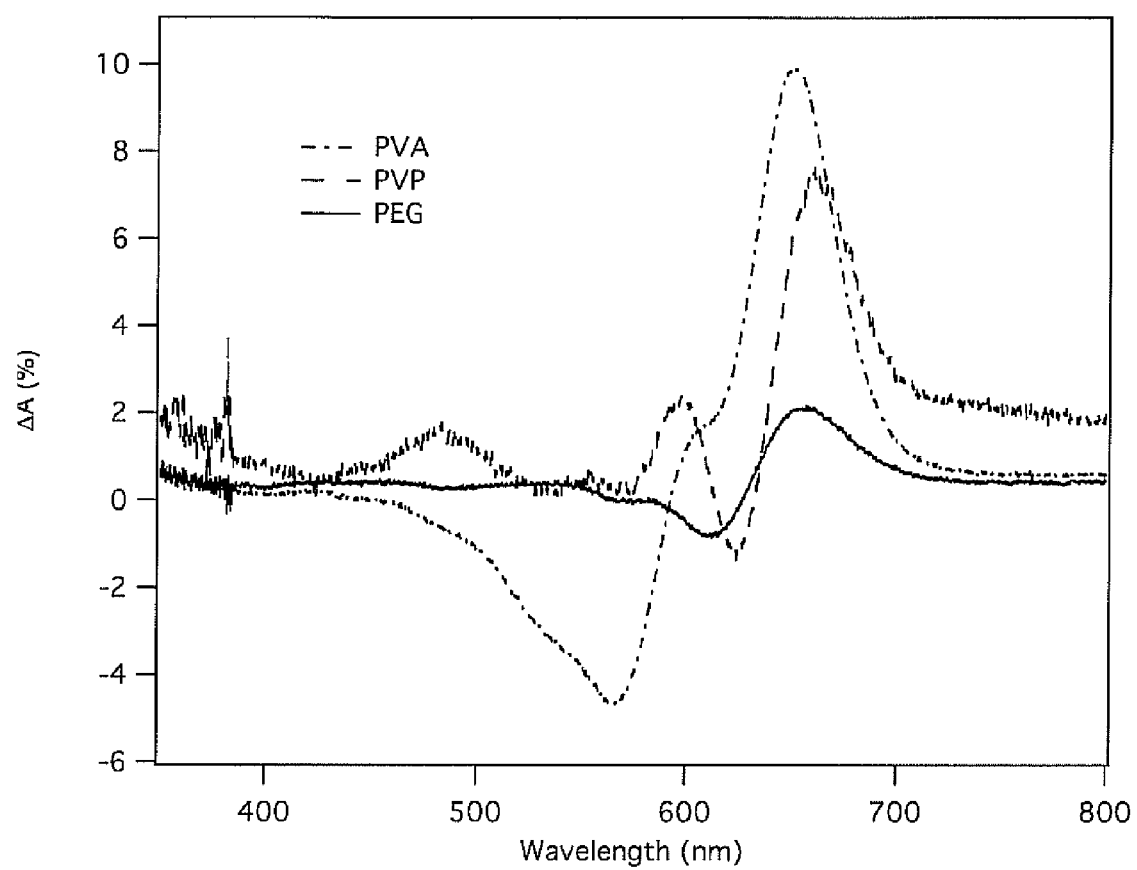
FIG. 4 graphically depicts the relative difference in the trypan blue spectra and demonstrates that trypan blue is more stable in a PEG solution.

The stability of trypan blue in a solution containing a hydrophilic polymer appears to be dependent on the nature of the polymer. FIG. 3 shows the normalized absorbance of a trypan blue solution (0.15% w/v end concentration) before and after being subjected to 70° C. for 7 days in the presence of 4% (w/v) of polyethylene glycol (PEG, Mw≈3350), 4% (w/v) polyvinyl alcohol (PVA, Mw≈13,000-23,000) and 4% (w/v) polyvinylpyrrolidone (PVP, Mw≈10,000), respectively. The relative difference spectra are compared in FIG. 4 (calculated by substracting the trypan blue spectra of FIG. 3), clearly demonstrating that trypan blue is more stable in PEG solution. In addition, it was found that in the presence of PVP a substantial amount of the original absorbance is lost.

Figure 5:
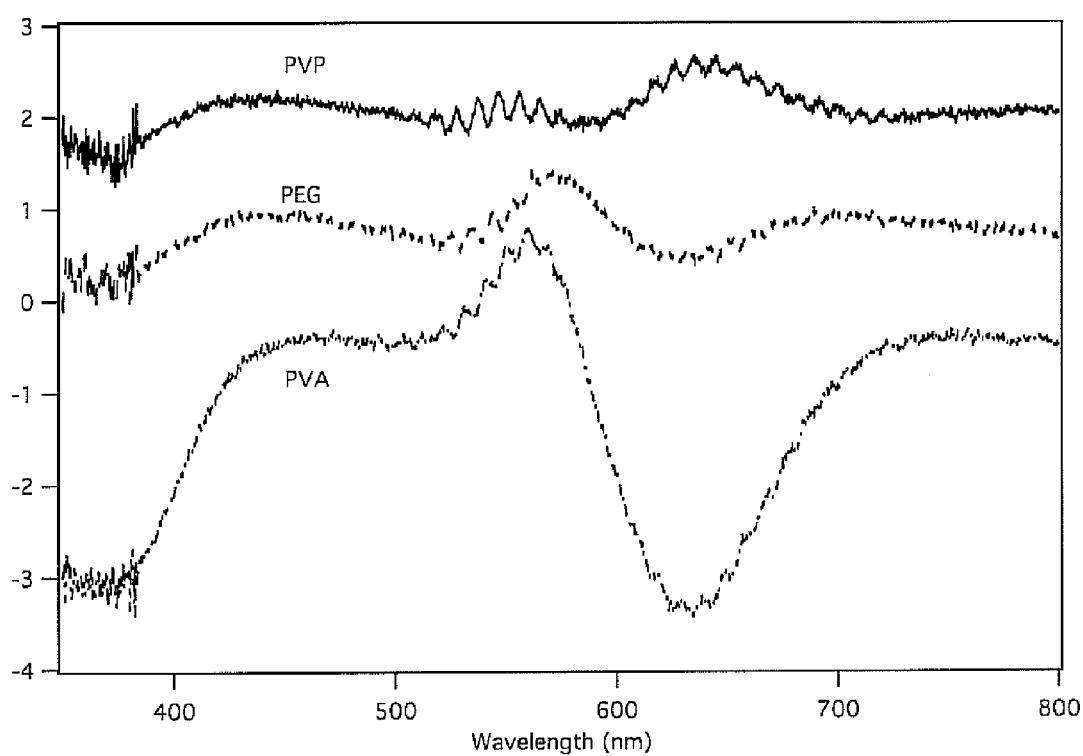
FIG. 5 graphically depicts the difference in absorbance spectra of brilliant blue G, before and after, stored at 70 degrees C. for 7 days in a solution containing polyethylene glycol (PEG).

Similar effects were observed for brilliant blue G, 0.025% (w/v), in these polymer containing solutions. FIG. 5 shows the difference absorbance spectra of brilliant blue G, 0.025% (w/v), before and after stored at 70° C. for 7 days in a solution containing 4% (w/v) of polyethylene glycol (PEG, Mw≈3350), polyvinyl alcohol (PVA, Mw≈13,000-23,000) and 4% (w/v) polyvinylpyrrolidone (PVP, Mw≈40.000). It appears that PEG is an excellent solvent for brilliant blue G. A similar result is observed for PVP, while brilliant blue G is much less stable in the presence of PVA.

The invention claimed is:

1. A method of treatment comprising,
    staining an ocular tissue or part of an ocular tissue with a staining composition,
    wherein the staining composition comprises a first and a second dye,
    wherein the first dye is trypan blue (TB) and the second dye is brilliant blue G (BBG), and
    wherein a concentration of polyethylene glycol in the staining composition is 2-10 wt. %.

2. The method according to claim 1, wherein the staining composition further comprises a density increasing compound and wherein the density increasing compound is an iodinated organic compound.

3. The method according to claim 1, wherein the polyethylene glycol has a molecular weight of 50-500,000 g/mol.

4. The method according to claim 1, wherein the weight ratio of the first dye to the second dye in the dye of the staining composition is between 1:1 and 100:1.

5. The method according to claim 1, wherein the staining composition further comprises a salt, wherein the salt is sodium chloride, potassium chloride, calcium chloride, magnesium chloride, or a combination thereof.

6. The method according to claim 1, wherein the staining composition is an aqueous solution, a colloidal dispersion or a viscous or viscoelastomeric solution, and wherein the concentration of the in the staining composition is 2-10 wt. %.

7. The method according to claim 4, wherein the staining composition has a density at 298 K of more than 1003 and less than 1040 kg*m$^{-3}$.

8. The method according to claim 4, wherein the staining composition has a viscosity of at least 2.0 mPa·s, as determined using a rheometer at 298 K.

9. The method according to claim 1, wherein the concentration of the first dye in the staining composition is 0.001-2 wt. %.

10. A method for preparing a staining composition, comprising the step of dissolving a first dye and a second dye,
    wherein the first dye is trypan blue (TB) and the second dye is brilliant blue G (BBG), and
    polyethylene glycol in a liquid; and dissolving a salt in the liquid to adjust the osmolarity of the liquid to a value between 250 and 400 mosmol/L.

11. The method according to claim 1, wherein the treatment is part of an eye surgery.

12. The method according to claim 2, wherein the density increasing compound is an iodixanol.

13. The method according to claim 2, wherein the density increasing compound is 5-N(N-2,3-dihydroxypropylacetamido)-2,4,6-tri-iodo-N,N'-bis(2,3-dihydroxypropyl) isophtalamide.

14. The method according to claim 1, wherein the polyethylene glycol has a molecular weight of 300-100,000 g/mol.

15. The method according to claim 1, wherein the polyethylene glycol has a molecular weight of 600-40,000 g/mol.

16. The method according to claim 1, wherein the weight ratio of the first dye to the second dye in the dye of the staining composition is between 2:1 and 25:1.

17. The method according to claim 1, wherein the weight ratio of the first dye to the second dye in the dye of the staining composition is between 4:1 and 15:1.

18. The method according to claim 1, wherein the staining composition is an aqueous solution, a colloidal dispersion or a viscous or viscoelastomeric solution, wherein the concentration of the polyethylene glycol in the staining composition is 3-6 wt. %.

19. The method according to claim 4, wherein the staining composition has a density at 298 K of more than 1004-1026 kg·m$^{-3}$.

20. The method according to claim 4, wherein the staining composition has a viscosity of at least 2.2 mPa·s, as determined using a rheometer at 298 K.

21. The method according to claim 4, wherein the staining composition has a viscosity of at least 2.5 mPa·s, as determined using a rheometer at 298 K.

22. The method according to claim 1, wherein the concentration of the first dye in the staining composition is 0.01-1 wt. %.

23. The method according to claim 1, wherein the concentration of the first dye in the staining composition is 0.1-0.5 wt. %.

24. The method according to claim 1, wherein the treatment is part of a vitreo-retinal surgery.

25. The method according to claim 1, wherein the treatment is part of a capsulorhexis procedure.

* * * * *